United States Patent [19]

Friebe et al.

[11] Patent Number: 5,716,983
[45] Date of Patent: Feb. 10, 1998

[54] USE OF COUMARINS AND CARBOSTYRILS AS $PLA_2$ INHIBITORS, NEW COUMARINS AND CARBOSTYRILS, PROCESSES FOR THE PRODUCTION THEREOF AND PHARMACEUTICAL AGENTS

[75] Inventors: Walter-Gunar Friebe; Wolfgang Schaefer, both of Mannheim; Werner Scheuer, Bad Tölz; Ulrich Tibes, Frankfurt, all of Germany

[73] Assignee: Boehringer Mannheim GmbH, Mannheim, Germany

[21] Appl. No.: 569,197

[22] PCT Filed: Jul. 9, 1994

[86] PCT No.: PCT/EP94/02251

§ 371 Date: Mar. 14, 1996

§ 102(e) Date: Mar. 14, 1996

[87] PCT Pub. No.: WO95/02588

PCT Pub. Date: Jan. 26, 1995

[30] Foreign Application Priority Data

Jul. 13, 1993 [DE] Germany .................. 43 23 409.7

[51] Int. Cl.⁶ .................. A61K 31/37; C07D 311/76
[52] U.S. Cl. .................. 514/457; 549/401
[58] Field of Search .................. 546/196, 207; 514/253, 320, 457; 424/281; 549/399, 401

[56] References Cited

U.S. PATENT DOCUMENTS

| | | | |
|---|---|---|---|
| 4,863,942 | 9/1989 | Wenk et al. | 514/381 |
| 5,124,334 | 6/1992 | Wilkerson | 514/277 |
| 5,534,533 | 7/1996 | Ohtani et al. | 514/372 |

*Primary Examiner*—C. Warren Ivy
*Assistant Examiner*—Charanjit S. Aulakh
*Attorney, Agent, or Firm*—Nikaido Marmelstein Murray & Oram LLP

[57] ABSTRACT

Use of compounds of formula I in which $R_1$, $R_2$, $R_3$, $R_4$, Y and Z have the meanings stated in the claims, tautomers thereof as well as their salts with non-toxic acids or bases for the production of pharmaceutical agents having an inhibitory action on $PLA_2$ in addition to compounds of formula I in which X does not denote a valency and processes for the production thereof.

8 Claims, No Drawings

USE OF COUMARINS AND CARBOSTYRILS AS PLA₂ INHIBITORS, NEW COUMARINS AND CARBOSTYRILS, PROCESSES FOR THE PRODUCTION THEREOF AND PHARMACEUTICAL AGENTS

This application is 371 of PCT/EP94/02251 which is now published as No. 95/02588.

The present invention concerns the use of coumarins and carbostyrils as PLA₂ inhibitors, new coumarin and carbostyril derivatives, processes for the production thereof and pharmaceutical agents which contain these compounds.

The invention concerns coumarin and carbostyril derivatives of the general formula I

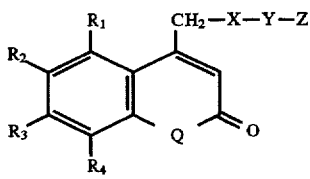

in which $R_1$ denotes hydrogen or $C_1$ to $C_6$ alkyl $R_2$ denotes hydrogen or a residue $OT_1$ or $R_1$ and $R_2$ together with the carbon atoms to which they are bound form a 3-membered to 7-membered carbocyclic ring $R_3$ denotes hydrogen or a residue $OT_2$ $R_4$ denotes hydrogen or $C_1$ to $C_6$ alkyl $T_1$ and $T_2$ which can be the same or different in each case denote $C_1$ to $C_6$ alkyl, $C_1$ to $C_6$ alkanoyl or $T_1$ and $T_2$, together with the atoms to which they are bound, form a 5-membered to 7-membered heterocyclic ring which can be substituted if desired with oxo or thioxo, or $R_3$ and $R_4$ together with the carbon atoms to which they are bound form a pyridine ring, Q denotes an oxygen atom or a NH group X denotes a valency bond, an oxygen or sulphur atom or a NH group Y denotes a valency bond, a $C_1$ to $C_6$ alkylene residue which can be substituted if desired with a hydroxyl group or an amino group, a phenylene residue which can be substituted if desired once or several times with hydroxyl, halogen, $C_1$ to $C_6$ alkyl or carboxyl denotes hydrogen, halogen, carboxyl, hydroxymethyl, $C_1$ to $C_6$ alkoxycarbonyl, cyano or a group $NR_5R_6$ in which $R_5$ and $R_6$ which can be the same or different, each represent hydrogen or $C_1$ to $C_6$ alkyl or $R_5$ and $R_6$ together with the nitrogen atom to which they are bound, form a 3-membered to 7-membered heterocyclic ring which can be substituted if desired with oxo, hydroxy or $C_1$ to $C_6$ alkoxy or contains a further heteroatom such as oxygen or sulphur their tautomers as well as salts thereof with non-toxic acids or bases.

Some of the compounds of formula I are known. Thus compounds of formula I are described in Chem. Abstr. 60, 4114b in which $R_1=R_4=H$, $R_2=R_3=OH$, Q=O, X=Y=valency and Z=$NR_5R_6$ as agents for the treatment of vascular diseases. In Chem. Abstr. 84, 159773k it is stated that such substances do not inhibit a carrageenin oedema.

Compounds in which $R_1=R_4=H$, $R_2$ and $R_3$=OH or alkyl =OH, Q=O, X=valency, A=alkylene and Z=hydrogen are described for example in Chem. Abstr. 68, 76748z as inhibitors of phenylalanine hydrolase; compounds in which $R_1=R_4=H$, $R_2$ and $R_3$ together are methylene-dioxy or $R_2=R_3=OCH_3$, Q=O, X=Y= valency and Z= carboxyl or alkoxycarbonyl are described in Chem. Abstr. 100, 31674k and 112, 151027 as fluorescent markers.

The synthesis of 4-methyl-6,7-dihydroxycoumarin is described in Chem. Ber. 34, 423 (1901). 4-Chloromethyl-6,7-dihydroxycoumarin is known from Chem. Abstr. 60, 4113 (1964) and Beilstein 18/3 V 233.

An anti-inflammatory action or specifically a PLA₂ inhibitor is not stated.

The compounds of formula I have valuable pharmacological properties and in particular they can inhibit the activity of phospholipases. Thus they are suitable for the treatment of acute and chronic, allergic, non-allergic and traumatic and inflammatory diseases such as for example rheumatoid arthritis, osteoarthritis, ulcerative colitis, acute pancreatitis, contact dermatitis, inflammatory and allergic respiratory tract diseases, septic shock, allergic shock, serum sickness, autoimmune diseases, graft-versus-host reactions, host-versus graft diseases, ischaemic or thrombotic diseases, such as coronary infarction or cerebral infarction.

Aklyl residues in the said groups alkyl, alkoxy and alkanol can be straight-chained or branched. Preferred residues are the methyl, ethyl, propyl, isopropyl, n-butyl, isobutyl, tert.-butyl, n-pentyl and 3-pentyl residue.

Alkylene residues can be straight-chained or branched. Preferred residues are methylene, 1,2-ethylene, 1,3-propylene, 1,2-propylene and 2,2-propylene.

Halogen atoms are in particular fluorine, chlorine and bromine.

Residues which enable $R_1$ and $R_2$ to together form a carbocyclic ring are preferred:

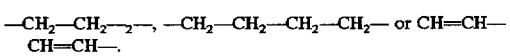

Residues which enable $R_2$ and $R_3$ to together form a heterocyclic ring are preferred:

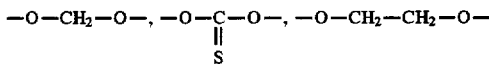

Residues which enable $R_5$ and $R_6$ to form a heterocyclic ring together with a nitrogen atom are preferred:

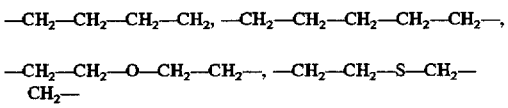

All substances which have every possible combination of the substituents stated in the examples are in particular a subject matter of the invention in addition to the compounds stated in the examples.

The invention also concerns new compounds of formula I in which X does not represent a valency bond as well as salts thereof with non-toxic acids or bases.

The process for the production of compounds of formula I according to the invention is characterized in that a compound of the general formula II

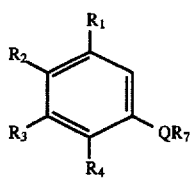

(II)

in which $R_1$ and $R_4$ and Q have the meanings stated above and $R_7$ represents hydrogen or a $C_1$ to $C_6$ alkanoyl residue is reacted in a known manner with a compound of the general formula III

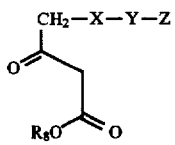

(III)

in which X, Y and Z have the meanings stated above and $R_8$ represents a $C_1$ to $C_6$ alkyl residue and it is cyclized, subsequently one or several residues $R_1$ to $R_4$, X, Y or Z are optionally converted into another residue as defined in the claim and it is optionally converted into a salt by neutralizing it with non-toxic acids or bases.

It is expedient to react compounds of formula II with compounds of formula III in an acidic medium such as diluted sulphuric acid or in a non-aqueous solvent in the presence of a Lewis acid such as zinc chloride or aluminium chloride while heating.

Subsequent optional conversion of one or several residues for example means cleaving an alkyl or alkanoyl residue which represents $T_1$ and/or $T_2$ by ether cleavage or hydrolysis or the introduction thereof by means of alkylation or esterification, replacing a halogen atom representing XYZ by nucleophilic substitution with formation of an O—YZ, NH—YZ or S—YZ group, a CN group or a group $NR_5R_6$, saponifying an alkoxycarbonyl or cyano group representing Z to form a carboxyl group, esterifying a carboxyl group representing Z to form an alkoxycarbonyl group reducing an alkoxycarbonyl or carboxyl group to form a hydroxymethyl group.

Compounds of formulae II and III are known from the literature or can be synthesized in a trivial manner from known precursors.

Alkaline, alkaline-earth and ammonium salts as well as salts with non-toxic inorganic or organic acids such as hydrochloric acid, sulphuric acid, phosphoric acid, hydrobromic acid, acetic acid, lactic acid, citric acid, malic acid, benzoic acid, salicylic acid, malonic acid, maleic acid, succinic acid or diaminocaproic acid come into particular consideration as pharmacologically tolerated salts.

Salts are obtained in the usual way by neutralizing compounds of formula I with appropriate lyes or acids.

For the production of pharmaceutical agents the compounds of the general formula I are mixed in a known manner with suitable pharmaceutical carrier substances, aromatics, flavourings and dyes and are formed for example into tablets or dragées or are suspended or dissolved in water or oil such as e.g. olive oil by addition of appropriate auxiliary substances.

Substances of the general formula I can be administered parenterally or orally in a liquid or solid form. Water can preferably be used as the injection medium which contains the common stabilizing agents, solubilizers and/or buffers for injection solutions. Such additives are for example tartrate or borate buffer, ethanol, dimethyl-sulfoxide, complexing agents (such as ethylene-diamine tetraacetic acid), high molecular polymers (such as liquid polyethylene oxide) to regulate viscosity or polyethylene derivatives of sorbitan hydrides.

Solid carriers are for example starch, lactose, mannitol, methylcellulose, talcum, highly dispersed silicic acid, higher molecular polymers (such as polyethylene glycols).

Preparations which are suitable for oral application can if desired contain flavourings and sweeteners. For external application the substances I according to the invention can also be used in the form of powders and ointments. For this they are for example mixed with physiologically tolerated diluents in the form of powders or conventional ointment bases. The administered dose depends on the age, health and weight of the recipient, the extent of the diseases, the type of additional treatments that may be carried out simultaneously, the frequency of treatments and the type of desired effect. The daily dose is usually 0.1 to 50 mg/kg body weight of active compound. 0.5 to 40 and preferably 1.0 to 20 mg/kg/day in one or several administrations per day are generally effective in order to obtain the desired results.

The following compounds are preferred within the sense of the invention apart from the substances stated in the examples:

6,7-dihydroxycoumarin-4-acetic acid [yield 35%, melting point 210°–212° C. (water)]

6,7-dihydroxy-4-(2-hydroxy-ethyl)coumarin 3-(6,7-dihydroxycoumarin-4-yl)propionic acid 6,7-dihydroxy-4-(2,3-dihydroxy-propoxy)methylcoumarin 3-(2-oxo-2H-pyrano[3,2-g]quinoline-4-yl-methyl-mercapto) propionic acid 3-(6-hydroxy-3-oxo-3,7,8,9-tetrahydro-cyclopenta[f][1]benzopyran-1-yl-methylmercapto)propionic acid 3-(6-hydroxy-3-oxo-7,8,9,10-tetrahydro-3H-naphtho[2,1-b]pyran-1-yl-methylmercapto)propionic acid 3-(6-hydroxy-3-oxo-3H-naphtho [2,1-b]pyran-1-yl-methylmercapto)propionic acid 3-(5-allyl-6-hydroxy-3-oxo-3H-naphtho[2,1-b]pyran-1-yl-methylmercapto)propionic acid 3-(6-hydroxy-3-oxo-5-propyl-3H-naphtho[2,1-b]pyran-1-yl-methylmercapto)propionic acid 3-(1,2-dihydro-2-oxo-quinoline-4-yl-methylmercapto)-propionic acid

EXAMPLE 1

4-methyl-6,7-dihydroxycoumarin 45 ml 75% sulphuric acid is added dropwise to a mixture of 5.8 ml ethyl acetate and 11.4 g 1,2,4-triacetoxy-benzene, heated for 30 min to 80° C., poured onto ice, filtered, the precipitate is washed neutral and dried in a vacuum. 8.2 g of the title compound (95 % of theory) is obtained with a melting point of 270° to 272° C.

EXAMPLE 2

In an analogous manner to that described in example 1 one obtains:

| | Name | Yield % | Melting point °C (solvent) |
|---|---|---|---|
| a) | 4-chloromethyl-6,7-dihydroxycoumarin from 1,2,4-triacetoxy-benzene and 4-chloroacetoacetic ester | 81 | 262 (ethanol) |
| b) | 4-bromomethyl-6,7-dihydroxycoumarin from 1,2,4-triacetoxybenzene and 4-bromoacetoacetic ester | 62 | 246–248 (ethanol) |
| c) | 4-(2-carboxy-phenylthio)methyl-6,7-dihydroxycoumarin from 1,2,4-triacetoxybenzene and 4-(2-carboxy-phenylthio)aceto-acetic ester | 52 | 275–277 (methanol) |
| d) | 4-bromomethyl-7-methoxycoumarin from 3-methoxy-phenol and 4-bromoacetoacetic ester | 47 | 205–207 (ether) |
| e) | 4-bromomethyl-6-methoxycoumarin from 4-methoxy-phenol and 4-bromoacetoacetic ester | 45 | 169–171 (ether) |
| f) | 4-bromomethyl-6,7-methylenedioxycoumarin from 3,4-methylenedioxyphenol and 4-bromoacetoacetic ester | 53 | 240–242 (methanol) |

EXAMPLE 3

4-N,N-dimethylaminomethyl-6,7-dihydroxycoumarin 5.7 g of the compound of example 2a is added to a solution of 4.5 g dimethylamine in 300 ml methanol, stirred overnight at room temperature, filtered, concentrated by evaporation and chromatographed on silica gel (eluting agent ethyl acetate: methanol 9:1). 3.3 g of the title compound is isolated (56% of theory) with a melting point of 212° to 215° C.

EXAMPLE 4

In an analogous way to that described in example 3 one obtains:

| | Name | Yield % | Melting point °C (solvent) |
|---|---|---|---|
| a) | 4-piperidinomethyl-6,7-dihydroxycoumarinhydrochloride from the compound example 2a and piperidine | 58 | 190–192 (acetone) |
| b) | 4-morpholinomethyl-6,7-dihydroxycoumarinhydrochloride from the compound example 2a and morpholine | 67 | above 270 (ethanol) |
| c) | 4-(4-methoxy-piperidino)methyl-6,7-dihydroxycoumarin hydrochloride from the compound example 2a and 4-methoxy-piperidine | 48 | 232–234 (ethnol) |
| d) | 4-(2-carboxy-phenylthio)methyl-6,7-dihydroxycoumarin from the compound example 2a and thiosalicylic acid | 45 | 275–277 (ethanol) |
| e) | 4-(ethoxycarbonylmethylthio)methyl-6,7-dihydroxycoumarin from the compound example 2a and mercaptoacetic acid ethyl ester | 64 | oil |
| f) | 4-(2-ethoxycarbonyl-ethylthio)methyl-6,7-dihydroxycoumarin from the compound example 2a and 3-mercaptopropionic acid ethyl ester | 58 | oil |
| g) | 4-(4-methoxy-piperidino)methyl-7-hydroxycoumarin from the compound example 8 and 4-methoxypiperidine | 81 | 151–153 (ether) |
| h) | 4-(e-carboxy-phenylthio)methyl-6,7-dihydroxycoumarin from the compound example 2a and 3-mercaptobenzoic acid | | |
| i) | 4-(4-carboxy-phenylthio)methyl-6,7-dihydroxycoumarin from the compound example 2a and 4-mercaptobenzoic acid | | |
| j) | 4-(2-carboxy-phenylthio)methyl-6-hydroxycoumarin from the compound example 7 and thiosalicylic acid | 52 | 262–264 (methanol) |
| k) | 4-(2-carboxy-phenylthio)methyl-7-hydrocoumarin from the compound of example 8 and thiosalicylic acid | 89 | 136–138 (water) |
| i) | 4-(2-carboxy-phenylthio)methyl-7-hydrocoumarin from the compound of example 2d and thiosalicylic acid | 45 | 238–240 (ethyl acetate) |
| m) | 4-(2-carboxy-phenylthio)methyl-6,7-methylenedioxy coumarin from the compound example 2f and thiosalicylic acid | | |
| n) | 4-(2-carboxy-phenoxy)methyl-6,7-dihydroxycoumarin from the compound example 2a and salicylic acid | | |
| o) | 4-(2,6-dicarboxy-phenylthio)methyl-6,7-dihydroxycoumarin from the compound example 2a and 2-mercapto-isophthalic acid | | |
| p) | 4-aminomethyl-6,7-dihydroxycoumarin from the compound example 2a and ammonia | | |
| q) | 4-(2-carboxy-anilino)methyl-6,7-dihydroxycoumarin from example 2a and anthranilic acid | | |
| r) | 4-(3-carboxy-anilino)methyl-6,7-dihydroxycoumarin from example 2a and 3-amino-benzoic acid | | |
| s) | 4-(4-carboxy-anilino)methyl-6,7-dihydroxycoumarin from example 2a and 4-amino-benzoic acid | | |
| t) | 4-hydroxymethyl-6,7-dihydroxycoumarin from the compound example 2a and water | 15 | 229–232 (water) |
| u) | 4-cyanomethyl-6,7-dihydroxycoumarin from the compound example 2a and sodium cyanide | 43 | 129–131 (ether) |
| v) | 2-(6,7-dihydroxycoumarin-4-yl-methylmercapto)ethanol from the compound example 2a and 2-mercapto-ethanol | 58 | 208–210 (ether) |
| w) | (L)-S-(6,1-dihydroxycoumarin-4-yl-methyl)cysteine from the compound example 2a and (L)-cysteine | 66 | 182–184 (water) |
| x) | 4-(6,7-dihydroxycoumarin-4-yl-methyl-mercapto)butyric acid from the compound example 2a and 4-mercapto-butyric acid | 34 | 163–165 (ethyl acetate) |
| y) | 4-(2-hydroxy-ethylamino)methyl-6,7-dihydroxycoumarin hydrochloride from the compound example 2a and ethanolamine | 34 | 225–227 (acetone) |
| z) | 4-(2-amino-ethylamino)methyl-6,7-dihydroxycoumarin hydrochloride from the compound example 2a and ethylene-diamine | 47 | 208–210 (water) |
| aa) | 4-n-butylaminomathyl-6,7-dihydroxycoumarin dihydroxychloride from the compound example 2a and n-butylamine | 28 | 218–220 (acetone) |
| ab) | 4-N,N-diethylaminomethyl-6,7-dihydroxycoumarin hydrochloride from the compound example 2a and diethylamine | 38 | 228–228 (acetone) |
| ac) | 4-(4-oxo-piperidino)methyl-6,7-dihydroxycoumarin hydrochloride from the compound example 2a and 8-aza-1,4-dioxaspiro[4,5]decane | 55 | 233–235 (water) |
| ad) | 4-([1-hydroxy-2-hexyl]amino)methyl-6,7-dihydroxycoumarin hydrochloride from the compound 2a and DL-2-amino-1-hexanol | 17 | 200–202 (acetone) |

EXAMPLE 5

6,7-dihydroxycoumarin-4-yl-methylmercaptoacetic acid

A mixture of 3.1 g of the compound of example 4e and 300 ml 50% acetic acid is heated for 24 hours to reflux. It is concentrated in a vacuum, taken up in diluted sodium bicarbonate solution, washed with ethyl acetate, the aqueous phase is acidified and the product is filtered. 2.1 g title compound (74% of theory) remains with a melting point of 254°–256° C.

EXAMPLE 6

In an analogous manner to that described in example 5 one obtains:

| Name | Yield % | Melt. point °C (solvent) |
|---|---|---|
| a) 3-(6,7-dihydroxycoumarin-4-yl-methylmercapto)propionic acid from the compound of example 4f | 72 | 234–236 (water) |

EXAMPLE 7

4-Bromomethyl-6-hydroxycoumarin

A mixture of 2.7 g of the compound of example 2e, 100 ml dichloromethane and 5.6 ml boron tribromide is stirred for 4 hours at room temperature, poured onto ice and the product is filtered. 1.8 g title compound (71% of theory) with a melting point of 198° to 200° C. is isolated.

EXAMPLE 8

4-Bromomethyl-7-hydroxycoumarin is obtained from the compound of example 2d analogously to example 7 in a yield of 70% and with a melting point of 182° to 184° C.

EXAMPLE 9

6,7-Diacetoxy-4-(4-methoxy-piperidino)methylcoumarin hydrochloride

A mixture of 1.5 g of the compound of example 4c and 15 ml acetic anhydride is heated for 2 hours to reflux. It is concentrated by evaporation, triturated with ether and the product is filtered. 1.4 g title compound (75%) with a melting point of 206° to 208° C. remains.

EXAMPLE 10

6,7-Dimethoxy-4-(4-methoxy-piperidino)methylcoumarin 1.1 ml dimethylsulfate is added to a solution of 1.5 g of the compound example 4c in 6 ml 2N sodium hydroxide solution and it is stirred overnight at room temperature. It is extracted with dichloromethane, dried and the extract is concentrated. 0.44 g of the title compound (30% of theory) remains with a melting point of 148° to 150° C.

EXAMPLE 11

8-(4-methoxy-piperidino)methyl-2-thioxo-1,3-dioxolo [4,5-g]coumarin 5 ml pyridine is added to a mixture of 1.5 g of the compound of example 4c and 40 ml chloroform and 1.12 ml thiophosgene dissolved in 10 ml chloroform is added dropwise at 20° C. It is stirred overnight at room temperature, the solution is washed with water, the organic phase is dried and purified on silica gel. 1.5 g of the title compound (88% of theory) is eluted with ethyl acetate which melts at 108° to 110° C. after trituration with ether.

EXAMPLE 12

4-(2-Carboxy-phenylthio)methyl-6,7-diacetoxycoumarin with a melting point of 216°–218° C. (ethyl acetate) is obtained in an analogous manner to that described in example 9 from the compound of example 2c in a 68% yield.

EXAMPLE 13

4-(2-Carboxy-phenylthio)methyl-6,7-dimethoxycoumarin is obtained in a 45 % yield from the compound of example 2c in an analogous manner to that described in example 10.

EXAMPLE 14

4-(2-Carboxy-phenylthio)methyl-6,7-ethylene-dioxycoumarin is obtained from the compound of example 2c and 1,2-dibromoethane in an analogous manner to that described in example 10.

Pharmacological tests

Effects of coumarins

The present application concerns pharmacological agents for the treatment of acute and chronic diseases with an inflammatory, immunological, allergic, non-allergic or traumatic genesis.

Since phospholipase $A_2$ ($PLA_2$) is a key enzyme in the development of these diseases, its inhibition is an effective remedy for these diseases.

Coumarins are inhibitors of $PLA_2$ whose profile of action is superior to that of the introduced antiphlogistic agents such as e.g. cyclooxygenease inhibitors. In order to compare the profiles of action indomethacin was selected as a typical cyclooxygenase inhibitor. The decrease of enzymatic activity measured as the cleavage of fatty acids from the sn-2 position of lecithin was measured as an indicator of $PLA_2$ inhibition.

Inhibition of $PLA_2$ activity

Human recombinant type II $PLA_2$ (=synovial $PLA_2$) was used for the tests as a typical representative of a $PLA_2$.

Table 1 shows the in vitro inhibition of this enzyme in percent by the representative compounds example 4c), example 5 and example 4w). The enzyme was inhibited dose-dependently up to 100%.

In contrast table 1 shows that indomethacin also inhibited the enzyme but only to a maximum of 52% at the highest concentration. This documents the superiority of the new $sPLA_2$ inhibitors compared to cyclooxygenase inhibitors.

TABLE 1

Inhibition of $sPLA_2$ enzyme activity by coumarin derivatives and indomethacin

| | Substances | | | |
|---|---|---|---|---|
| Concentration | examp. 4c) | examp. 5 | examp. 4w) | indomethacin |
| 100 µg/ml | 86 | n.d. | n.d. | 52 |
| 10 µg/ml | 89 | 97 | 95 | 10 |
| 1 µg/ml | 34 | 49 | 37 | 0 |
| 0.1 µg/ml | 6 | 9 | 4 | n.d. |

Mean values from 4 experiments (duplicate determinations), n.d. = not determined Conclusion The lower inhibition of human recombinant type II $PLA_2$ by indomethacin illustrates that this cyclooxygenase inhibitor only has a weak inhibitory action on $PLA_2$. In contrast the coumarin representatives examp. 4c), examp. 5 and examp. 4w) inhibited $PLA_2$ dose-dependently by up to 100% and are superior to introduced anti-inflammatory agents.

We claim:

1. A method of inhibiting $PLA_2$ in a patient in need of such inhibition, comprising administering to the patient an effective amount of a compound of the formula

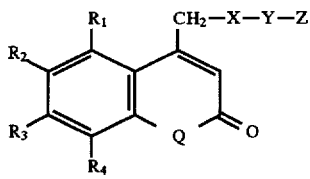

wherein $R_1$ is hydrogen, $R_2$ is a residue $OT_1$, $R_3$ is a residue $OT_2$, $R_4$ is hydrogen, $T_1$ and $T_2$ are independently hydrogen, $C_1-C_6$ alkyl or $C_1-C_6$ alkanoyl, or $T_1$ and $T_2$, together with the atoms to which they are bound, form a 5- to 7-membered heterocyclic ring which is unsubstituted or is substituted by oxo or thioxo, Q is an oxygen atom, X is a sulfur atom or a NH group, Y is (a) a $C_1-C_6$ alkylene residue which is unsubstituted or is a substituted by a hydroxyl group or an amino group, or (b) a phenylene residue which is unsubstituted or is substituted at least once by hydroxyl, halogen, $C_1-C_6$ alkyl or carboxyl, Z is halogen, carboxyl, hydroxymethyl, $C_1-C_6$ alkoxycarbonyl, cyano or a group $NR_5R_6$ wherein $R_5$ and $R_6$ are independently hydrogen or $C_1-C_6$ alkyl, or $R_5$ and $R_6$, together with the nitrogen atom to whyich they are attached, form a 3- to 7-membered heterocyclic ring which is unsubstituted or is substituted by oxo, hydroxy or $C_1-C_6$ alkoxy, or a tautomer thereof or a salt thereof with a non-toxic acid or base.

2. The method of claim 1, wherein the compound is selected from the group consisting of (L)-S-(6,7-dihydroxycoumadn-4-yl-methyl) cysteine, 4-(4-methoxy-piperidino) methyl-6,7-dihydroxycoumarin and 6,7-dihydroxycoumarin-4-yl-methylmercapto acetic acid.

3. A compound of the formula

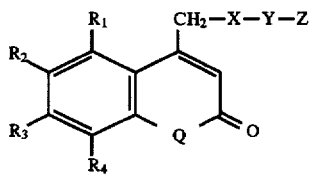

wherein $R_1$ is hydrogen, $R_2$ is a residue $OT_1$, $R_3$ is a residue $OT_2$, $R_4$ is hydrogen, $T_1$ and $T_2$ are independently hydrogen, $C_1-C_6$ alkyl or $C_1-C_6$ alkanoyl, or $T_1$ and $T_2$, together with the atoms to which they are bound, form a 5- to 7-membered heterocyclic ring which is unsubstituted or is substituted by oxo or thioxo, Q is an oxygen atom, X is a sulfur atom, Y is (a) a $C_1-C_6$ alkylene residue which is unsubstituted or is a substituted by a hydroxyl group or an amino group, or (b) a phenylene residue which is unsubstituted or is substituted at least once by hydroxyl, halogen, $C_1-C_6$ alkyl or carboxyl, Z is carboxyl, hydroxymethlyl or $C_1-C_6$ alkoxycarbonyl, or a tautomer thereof or a salt thereof with a non-toxic acid or base.

4. The compound of claim 3, wherein the compound is selected from the group consisting of (L)-S-(6,7-dihydroxycoumarin-4-yl-methyl) cysteine and 7-dihydroxycoumarin-4-yl-methylmercapto acetic acid.

5. 4-(4-methoxy-piperidino) methyl-6, 7-dihydroxycoumarin, or a tautomer thereof or a salt thereof with a non-toxic acid or base.

6. A pharmaceutical composition suitable for the inhibition of $PLA_2$, comprising a compound of the formula

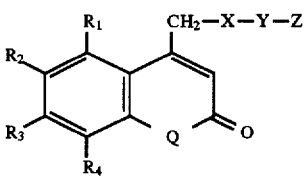

wherein $R_1$ is hydrogen, $R_2$ is a residue $OT_1$, $R_3$ is a residue $OT_2$, $R_4$ is hydrogen, $T_1$ and $T_2$ are independently hydrogen, $C_1-C_6$ alkyl or $C_1-C_6$ alkanoyl, or $T_1$ and $T_2$ together with the atoms to which they are bound, form a 5- to 7-membered heterocyclic ring which is unsubstituted or is substituted by oxo or thioxo, Q is an oxygen atom, X is a sulfur atom, Y is (a) a $C_1-C_6$ alkylene residue which is unsubstituted or is a substituted by a hydroxyl group or an amino group, or (b) a phenylene residue which is unsubstituted or is substituted at least once by hydroxyl, halogen, $C_1-C_6$ alkyl or carboxyl, Z is carboxyl, hydroxymethyl or $C_1-C_6$ alkoxycarbonyl, or a tautomer thereof or a salt thereof with a non-toxic acid or base, and a pharmaceutically acceptable carrier.

7. The pharmaceutical composition as claimed in claim 6, wherein the compound is selected from the group consisting (L)-S-(6, 7-dihydroxycoumarin-4-yl-methyl) cysteine and 6, 7-dihydroxycoumarin-4-yl-methylmercapto acetic acid.

8. A pharmaceutical composition suitable for the inhibition of $PLA_2$, comprising 4-(4-methoxy-piperidino) methyl-6, 7-dihydroxycoumarin, or a tautomer thereof or a salt thereof with a non-toxic acid or base, and a pharmaceutically acceptable carrier.

* * * * *